United States Patent [19]

Travis, III

[11] Patent Number: 5,046,329

[45] Date of Patent: Sep. 10, 1991

[54] PORTABLE AIR CONDITIONING UNIT

[76] Inventor: John P. Travis, III, 8820 Southwestern Blvd., #1109, Dallas, Tex. 75206

[21] Appl. No.: 358,553

[22] Filed: May 26, 1989

[51] Int. Cl.⁵ .......................................... F25D 23/12
[52] U.S. Cl. ..................................... 62/259.3; 62/406
[58] Field of Search ..................... 62/259.3, 406, 529, 62/530, 3.5, 3.62

[56] References Cited

U.S. PATENT DOCUMENTS

| | | | |
|---|---|---|---|
| 521,795 | 6/1894 | Hughes | 62/239 |
| 433,942 | 8/1890 | Hughes | 165/42 |
| 2,109,310 | 2/1938 | Cordrey | 62/239 |
| 2,159,406 | 5/1939 | Schwebs | 62/239 |
| 2,557,004 | 6/1951 | Lepper | 62/239 |
| 2,724,951 | 11/1955 | Arce | 62/337 |
| 3,043,116 | 7/1962 | Fuller | 62/337 |
| 3,074,250 | 1/1963 | Everett | 62/259.3 |
| 3,164,971 | 1/1965 | Gentz | 62/406 X |
| 3,224,218 | 12/1965 | New | 62/338 |
| 3,353,191 | 11/1967 | Dahly | 62/259.3 X |
| 3,529,435 | 9/1970 | Becker | 62/244 |
| 3,548,415 | 12/1970 | Waters | 62/259.3 X |
| 3,774,410 | 11/1973 | Hans | 62/406 X |
| 3,916,639 | 11/1975 | Atkinson | 62/337 |
| 3,961,496 | 6/1976 | Ku | 62/244 |
| 4,177,652 | 12/1979 | Volk | 62/239 |
| 4,637,222 | 1/1987 | Fujiwara | 62/244 |
| 4,765,151 | 8/1988 | Bessey | 62/239 |
| 4,860,556 | 8/1989 | Hammett | 62/406 |

FOREIGN PATENT DOCUMENTS 2122336 1/1984 United Kingdom ................. 62/406

Primary Examiner—Lloyd L. King
Attorney, Agent, or Firm—Richards, Medlock & Andrews

[57] ABSTRACT

Two versions of a portable air conditioning unit (10, 100) are provided. The larger unit (10) is separable into two halves (12, 14) which contain three cold objects (32, 34, 36) such as freezable gels. A series of aluminum baffles (22-30) define a torturous air flow passage through the unit where air passes over each one of the cold objects sequentially to significantly cool the air flow through the unit. The air flow is generated by a fan (38) which can be powered by batteries, AC power, solar power or the like. The second embodiment of the air conditioning unit (100) can be actually carried by the user with a strap to cool the face of the user.

4 Claims, 4 Drawing Sheets

PORTABLE AIR CONDITIONING UNIT

TECHNICAL FIELD

This invention relates to an air conditioning unit, and specifically to a portable unit for carrying by an individual.

BACKGROUND OF THE INVENTION

An air conditioned environment is important to personal comfort and even health. The most common air conditioning units controlled by individuals are the home air conditioner, usually a central electric unit or electric window air unit, and the automobile air conditioner.

As is well known, air conditioning a room or house electrically becomes quite expensive. Many people, particularly elder people on a fixed budget, can not afford to run the air conditioning. As a result, many elderly people must suffer through the summer heat at risk to their very health.

Even if one is financially secure to run a home air conditioning unit, and pay for the extra gasoline necessary to run an automobile air conditioning unit, those units are by their very nature only effective at the home or when in the car. A conventional air conditioning system, usually requiring a source of power, a compressor, an evaporator, a fan, and a condenser, is dearly impractical for portable use.

SUMMARY OF THE INVENTION

In accordance with one aspect of the present invention, a portable cooling unit is provided which includes a case, preferably insulating, defining a passage therethrough opening to the ambient air at an inlet and an outlet. A cold object having a temperature less than the temperature of the ambient air is positioned in the passage. A fan forces ambient air through the passage from the inlet, past the cold object, and discharges the air out the outlet at a lowered temperature.

In accordance with another aspect of the present invention, a plurality of cold objects can be used in the unit, for example three, and the passage can be a torturous one (i.e. a long passage with the air remaining in the passage as long as possible) to provide maximum cooling of the air travelling through the passage. The cold objects can be frozen blocks of ice or other material. Aluminum plates can be used not only to guide the air through the passage but also as thermal conductors to enhance the cooling.

In accordance with another aspect of the present invention, the cooling unit can be made with a two-part case which can be disassembled to place the cold objects therein. The unit can also be small enough to be hung around a person's neck, for example, while jogging or walking.

BRIEF DESCRIPTION OF THE DRAWINGS

For a more complete understanding of the present invention and for further advantages thereof, reference is now made to the following Detailed Description taken in conjunction with the accompanying drawings, in which.

DETAILED DESCRIPTION

Referring to FIG. 1–5, a portable air conditioning unit 10 is disclosed which generally provides for cooling of an airstream for user comfort, while requiring very little, if any, external power and being light enough to carry to the beach, in the car, or elsewhere.

Figure 2:
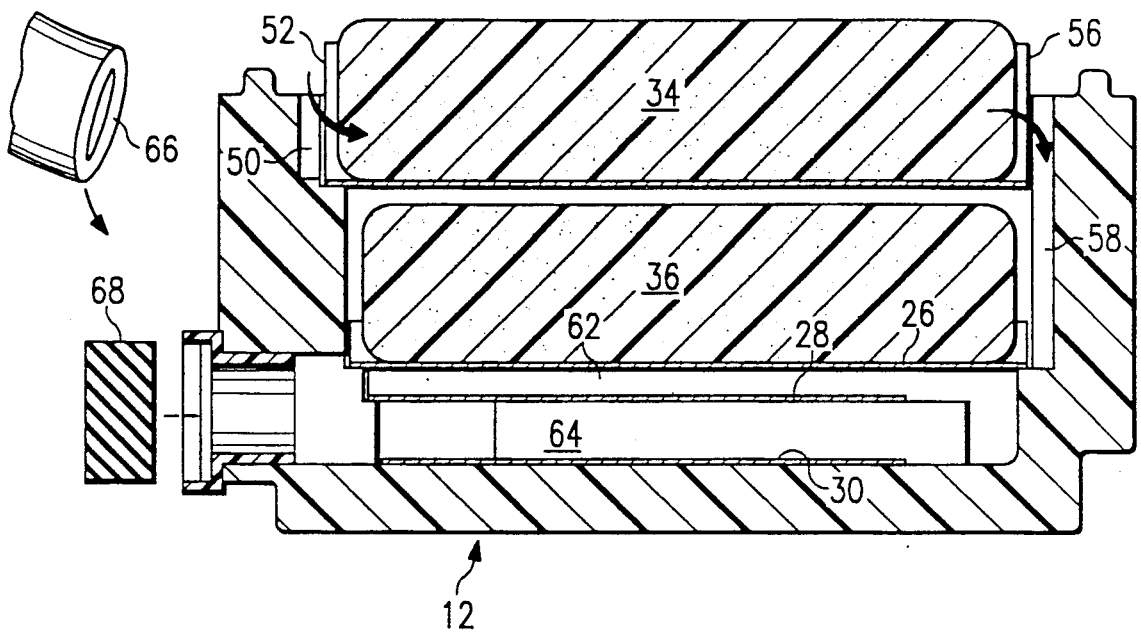
FIG. 2 is a vertical cross sectional view of the lower half of the unit.
Figure 3:
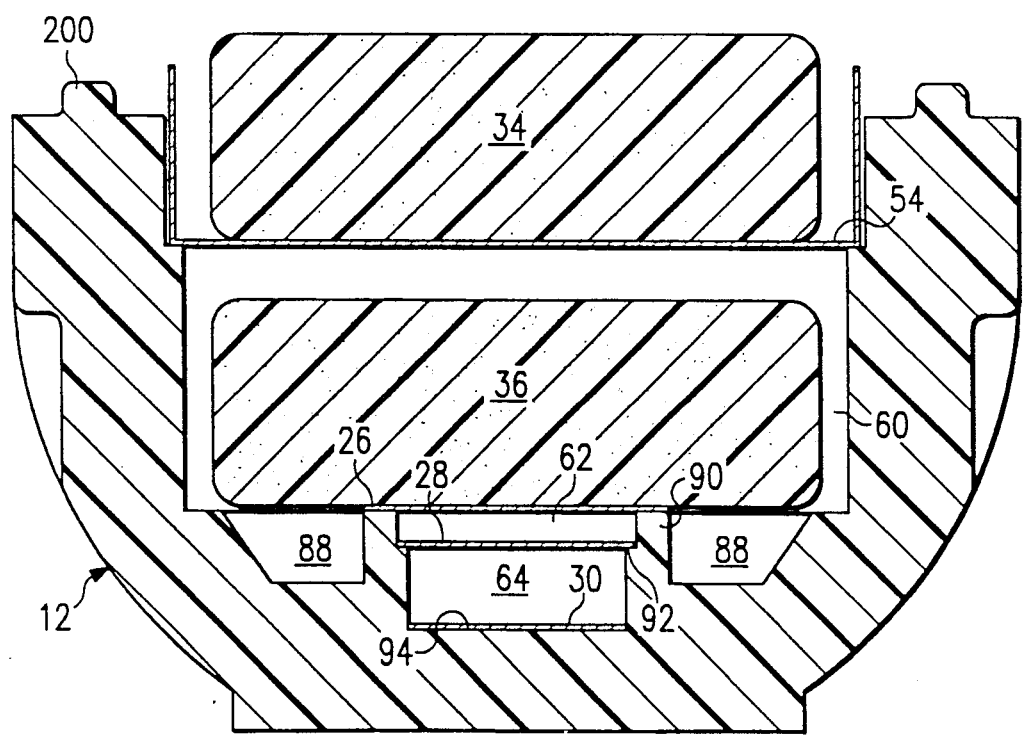
FIG. 3 is a vertical cross sectional view of the lower half of the unit.
Figure 4:
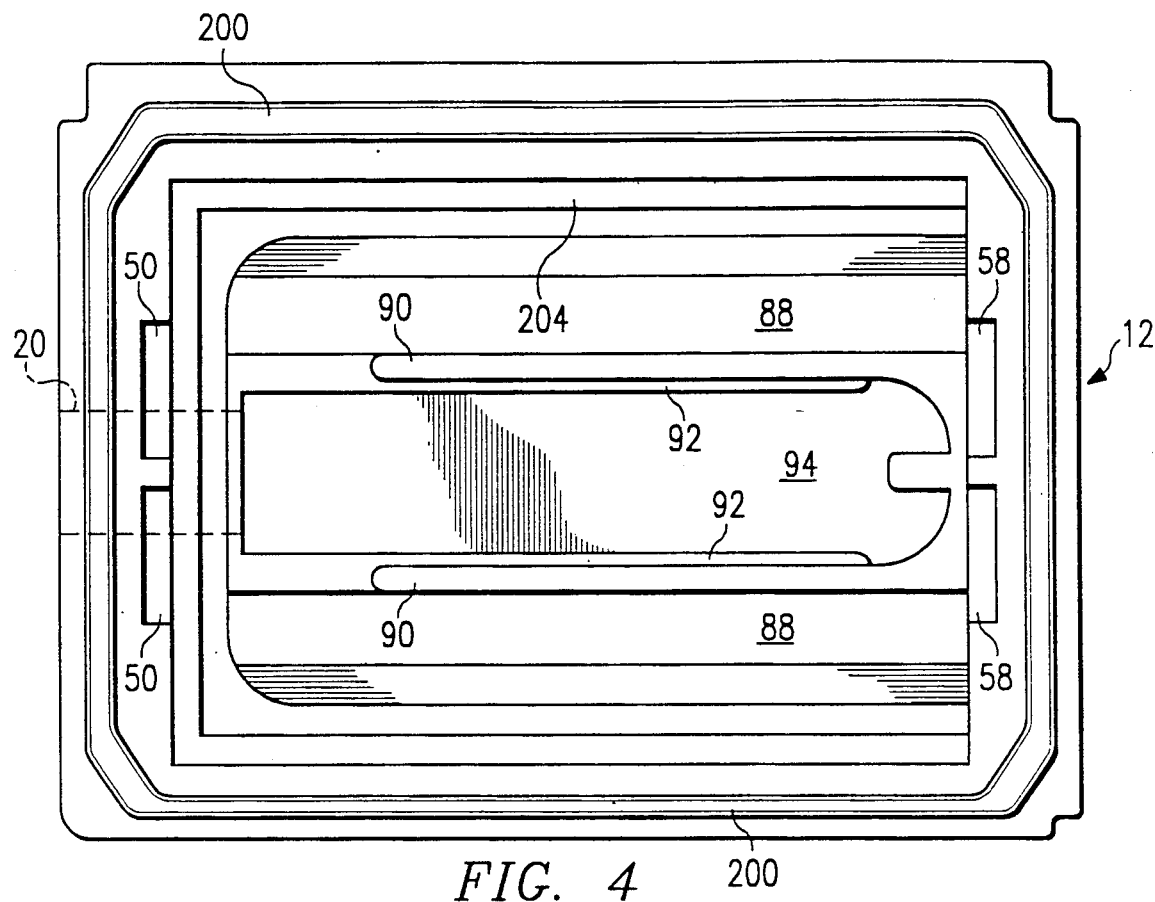
FIG. 4 is a plan view of the lower half.
Figure 5A:
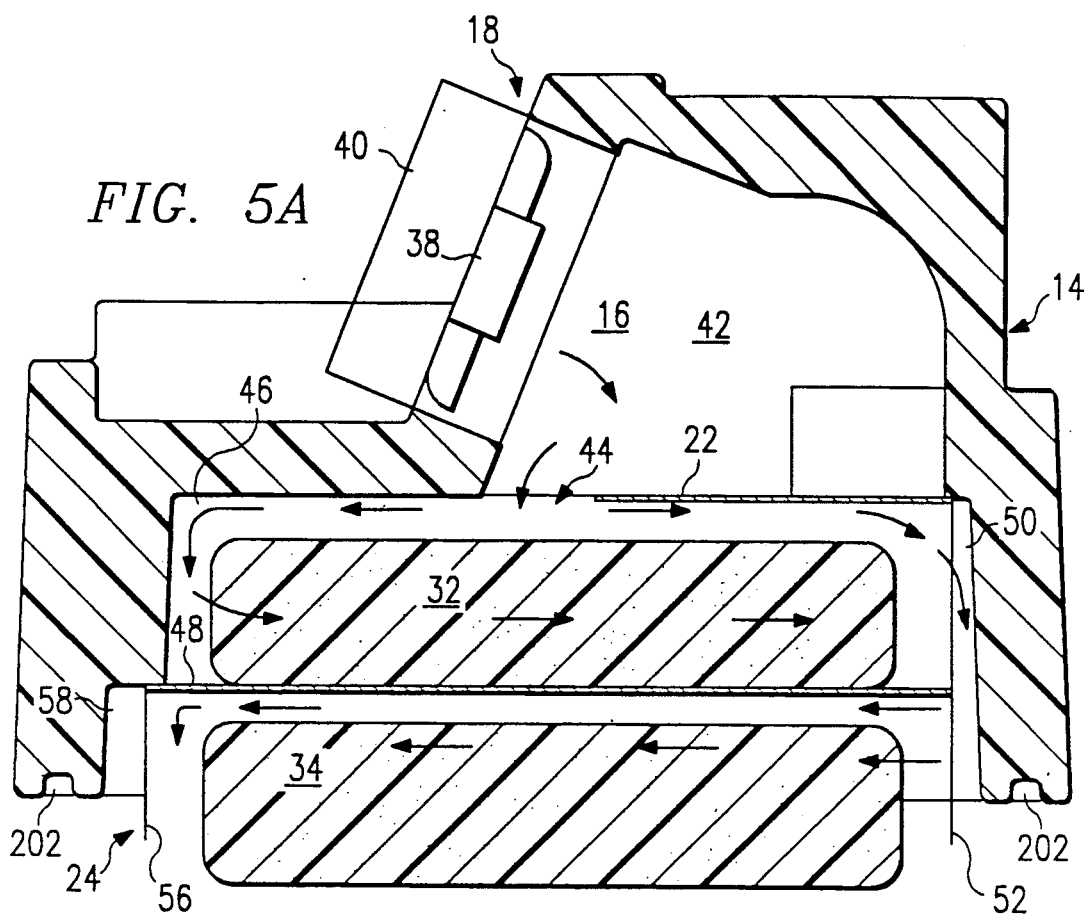
FIGS. 5A and 5B are vertical cross sectional views of the upper half of the unit.
Figure 5B:
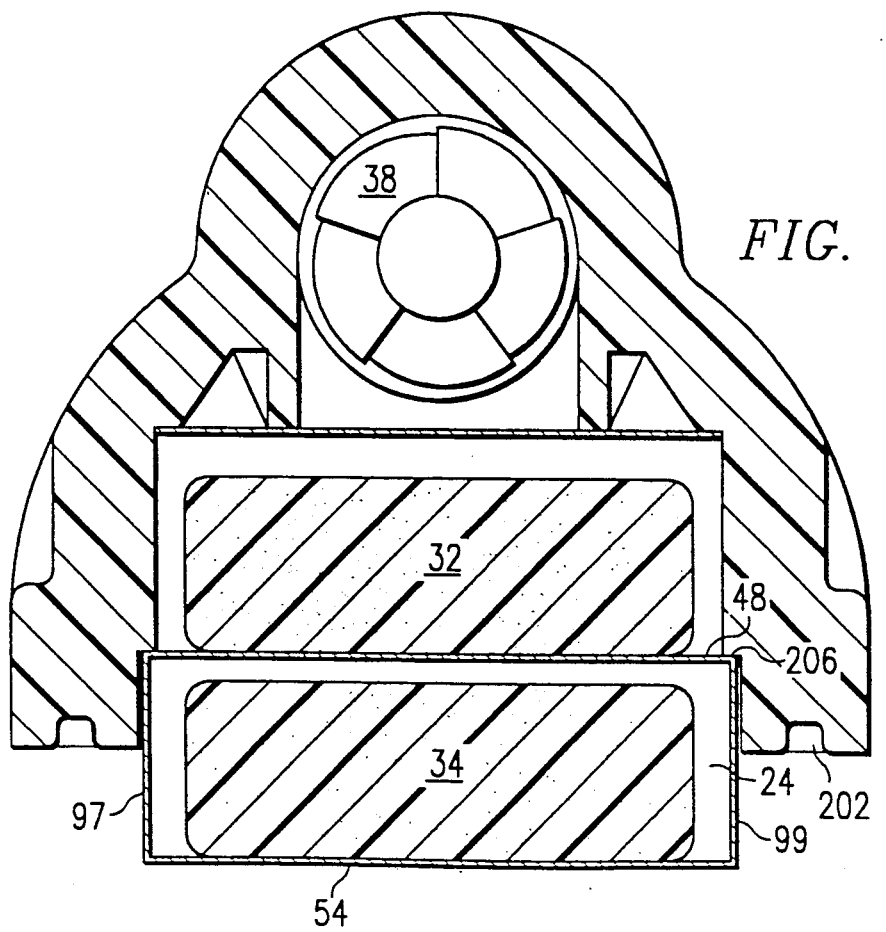

The unit includes a lower half 12, shown in FIG. 2–4, and an upper half 14, shown in FIG. 5. When 10 positioned together, the lower and upper halves 12 and 14 define a long air flow passage 16 through the unit which extends from an air inlet 18 to an air outlet 20. Preferably, halves 12 and 14 snap fit together with tongue 200 and groove 202 in an airtight manner. As will be discussed in greater detail, the internal configuration of the halves 12 and 14, along with the presence of five metal baffles, 22–30, define the passage.

Within the air flow passage are positioned three cold objects, objects 32, 34 and 36, which rest on various of the baffles. Air flow passing through the passage from the inlet to the outlet passes over each of the cold objects sequentially to cool the air. Thus, the air that issues from the outlet 20 has been cooled to a degree determined by the various heat transfer characteristics of the components of the unit.

With reference to FIG. 5, a fan 38 can be seen to be mounted at the air inlet 18. Fan 38 is shown to be powered by a conventional AC motor 40 with a power cord to connect directly to a wall outlet. Alternatively, the fan 38 can be run from internal battery power or solar cells to make the unit completely portable. Whether powered by an external source, or an internal power source, the fan 38 will drive ambient temperature air into the inlet 18 into cavity 42 within the upper half 14. An aluminum or galvanized steel baffle 22 guides the air flow through a small passage 44 into a chamber 46 containing a first cold object 32. The air is cooled by passage over the cold object 32 as it flows about the object as illustrated by the arrows in FIG. 5. The top 48 of a ductlike aluminum baffle 24 supports the cold object 32 and ensures that the air flow enters a passage 50 at the right end of the upper half as shown in FIG. 5 (baffle 24 has top 48, bottom 54, and sides 97 and 99).

Passage 50 directs the air flow downwards and through the open end 52 of the aluminum baffle 24. The air then flows over the second cold object 34 to be further cooled as the air moves from the right side of the upper half to the left side of the upper half as shown in FIG. 5. The bottom 54 of the aluminum baffle 24 supports the second cold object 34.

After passing over the second cold object, the air flow passes through the open end 56 of the aluminum baffle 24 and downward through a passage 58 formed partly in the upper half 14 and partly in the lower half 12. The air then flows into a chamber 60 containing the third cold object 36 and flows over that object, being further cooled. The third cold object is supported by aluminum baffle 26. From chamber 60, the air flow continues down notches 88 formed on either side of chamber 60 near the outlet end of the case (on the left as seen in FIG. 4) and then through a passage 62 defined between aluminum baffle 26 and aluminum baffle 28. Baffle 26 rests on ledges 90 of lower half 12. Baffle 28 rests on ledges 92 of lower half 12. Finally, the air flow passes through a passage 64 defined between aluminum baffle 28 and aluminum baffle 30 before being discharged from the air outlet 20. Baffle 30 rests on the bottom inner surface 94 of lower half 12.

The cold objects can be any suitable object, substance or form which is cooler than the ambient air and provides for adequate cooling of the air for whatever function the unit 10 is intended. For example, the cold objects could be formed by freezable containers of water or gel which can be placed in a home freezer unit and frozen. For example, each cold object could comprise a 56 oz bag of a freezable, reusable gel such as sold by Van Waters & Rogers in Dallas, Texas, sealed in a fluid tight bag.

While the baffles 24-30 are disclosed as being aluminum, and baffle 22 of galvanized steel or aluminum, other conductive, non-corrosive metallic or non-metallic materials can be used such as copper, galvanized steel, etc. If one does not wish to take advantage of the conductivity of the baffles, non conductive, moisture resistant materials could be used for the baffles such as treated cardboard, plastic, etc. However, aluminum is a very good heat conductor, is light, and greatly assists in cooling of the air as it flows through the passage 16. Halves 12 and 14 are preferably formed of EPS (expanded polystyrene) with a hard, smooth, easily cleanable plastic skin 304 sprayed or molded on the outer surface thereof. Skin 304 also adds to the insulating ability of the unit, preventing, for example, air flow through the EPS. Plastic skin 304 could be vinyl, for example. Cloth or fabric wrap could be used as a less satisfactory substitute for skin 304. As can be readily understood, the upper and lower halves are readily separable to gain access to the cold objects 32, 34 and 36. The cold object 32 will be exposed simply by removing the upper half 14. The second cold object can be removed by simply removing the aluminum baffle 24 from the lower unit, in which it simply sits, and sliding the object 34 out of one of the open ends of the baffle 24. Removal of baffle 24 also then exposes the third cold object 36. Baffle 24 sits on ledge 204 of lower half 12 and against ledge 206 on upper half 14. The objects can be frozen or otherwise cooled prior to use of the unit, installed in the unit and then used to cool air flowing through the unit for whatever period of time the objects can cool the air.

In a unit constructed in accordance with the teachings of the present invention, a 35° F. drop in air temperature has been achieved between inlet and outlet air for an air flow of about 184 cu.ft./minute. Using three 56 oz reuseable gel bags, the unit was able to cool air significantly for a period of eight to ten hours. At the end of eight hours, the temperature drop was about 12° F. The upper and lower halves were made of EPS (expanded polystyrene) plastic of 2 pounds/cu.ft. density in a molding process. The aluminum was 0.020" thick. The entire unit, with cold objects, weighs only 14½ pounds.

In the unit, which is only about 10 to 11 inches in interior length, the passage is 80 inches long, with the baffles causing the air to travel this long distance to maximize cooling.

Various accessories can be provided for the unit 10. For example, the fan 38 can be made as an attachment to the unit, so that a user can purchase both a battery operated fan and an AC operated fan and use the fans interchangeably for whatever purpose the unit is used at a given time. Further, a hose 66, such as shown in FIG. 2, can be used to direct the cooled air to a specific area. Hose 66 is preferably made of insulating material. Plugs 68 can be inserted in the inlet and outlet when the unit is not in use to maximize life of the cold objects.

It will be appreciated that the portable air conditioning unit 10 has uses which are only limited by the imagination. The unit can be used on the nightstand of the bed to provide for comfortable sleeping throughout the night. This may permit the sleeper to totally eliminate use of the central air conditioning unit in the house or a window mounted unit, or to supplement those units. In either event, the cost of freezing the objects 32-36 in the home freezer is so low that there is a significant cost savings versus various types of air conditioning in the home. The unit 10 can be taken on auto trips, to supplement or substitute for the automobile air conditioner, to the beach, to picnics, or any other use where a portable unit of this type may be of benefit.

Figure 1:
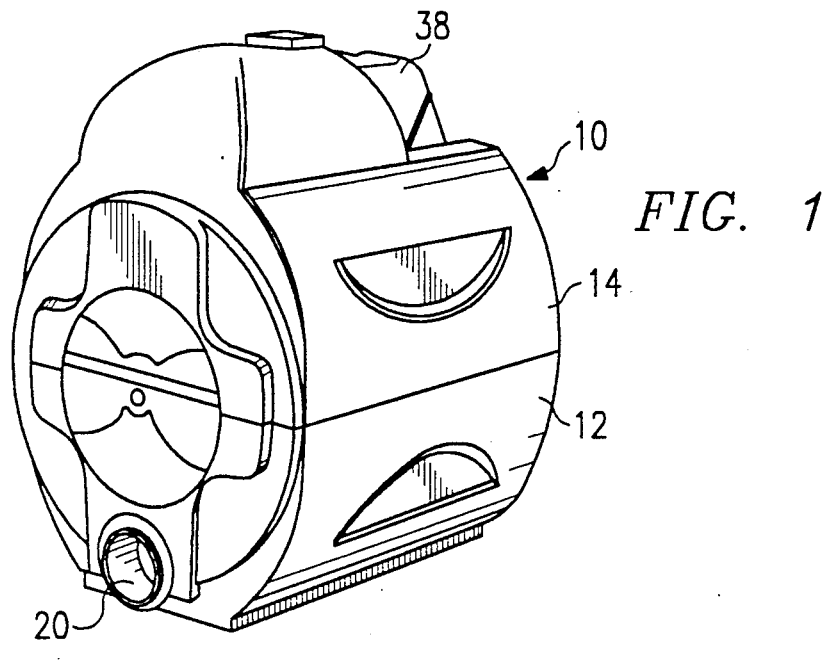
FIG. 1 is a perspective view of an air conditioning unit forming a first embodiment of the present invention.
Figure 6:
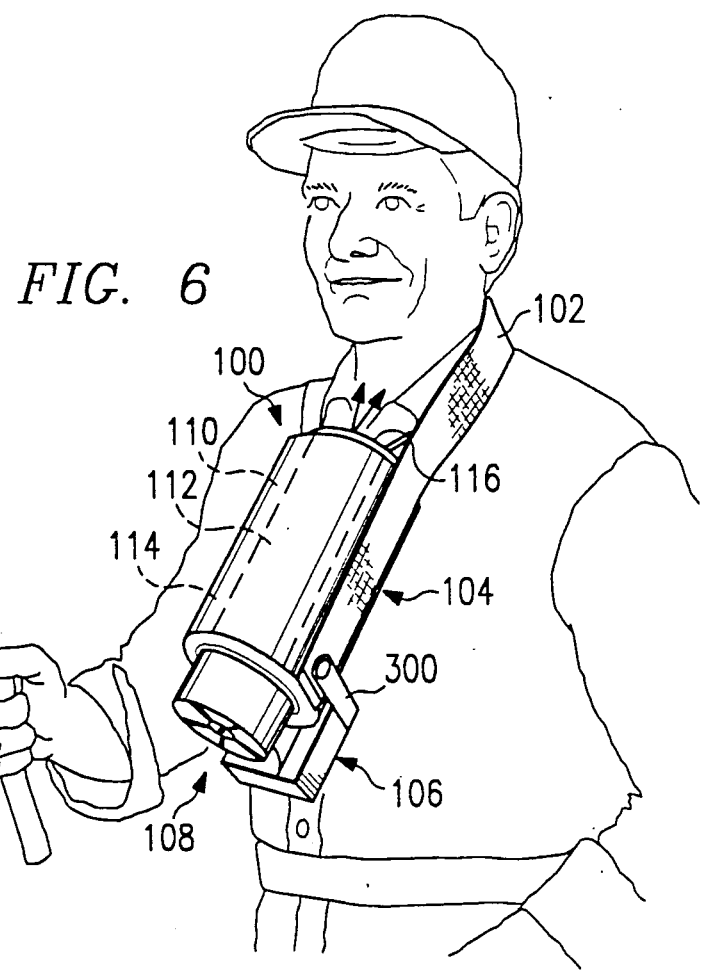
FIG. 6 is a perspective view of a portable air conditioning unit forming a second embodiment of the present invention.
Figure 7:
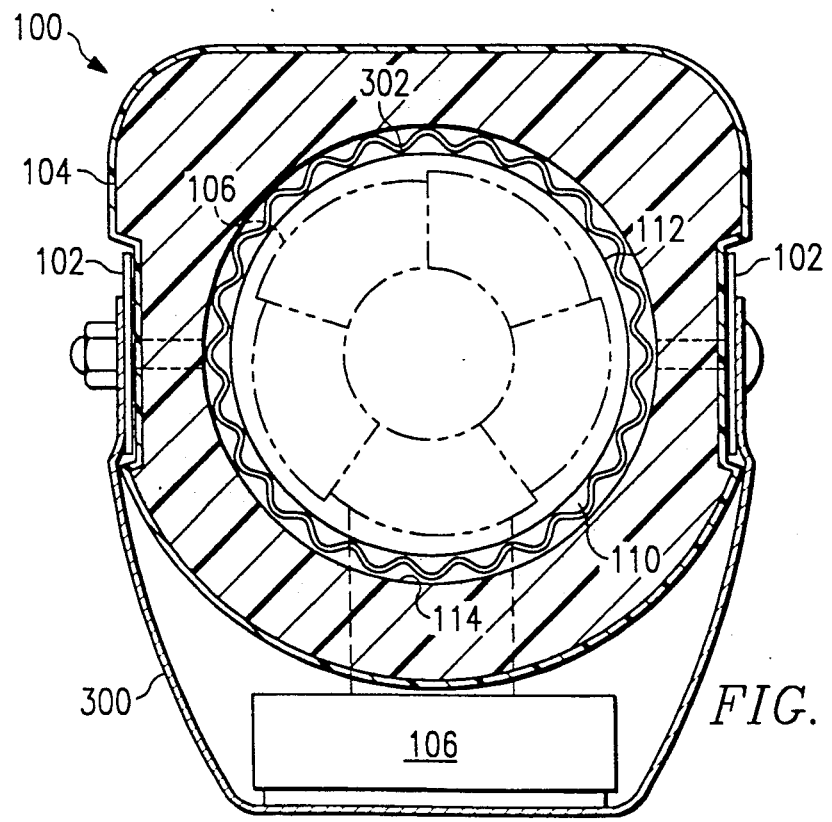
FIG. 7 is a cross sectional view of the unit of FIG. 6.

With reference now to FIGS. 6 and 7, a portable air conditioning unit 100, forming a second embodiment of the present invention is illustrated. The operating principles of unit 100 are identical to those of unit 10, but unit 100 is designed to be so light and compact as to be worn around the neck of an individual with a strap 102. The unit 100 thus would provide direct cooling to the individual's face, and can be used while jogging, working outdoors in the sun, or at a sporting event, or at any time that such a unit would be of assistance. The case 104 of the unit 100 is also preferably formed of EPS shaped or molded plastic, with an outer plastic skin 304, as unit 10, to provide a smooth and easily cleaned surface (skin 304 also seals the EPS to make it airtight). A fan unit 106 is mounted on the case by strap 300 which contains a small fan and battery pack, preferably rechargeable. Air is drawn into inlet 108 by the fan unit and passes in the annular chamber 110 between a cold (freezable) jar 112 in the unit 100 and the inner wall 114 of the case before discharging out outlet 116. An aluminum corrugated duct 302 preferably extends the length of chamber 110 to enhance air cooling. Duct 302 preferably touches the jar at various points to enhance the heat transfer. Cold jar 112 can be removed from the remainder of unit 100. While the cold jar 112 could be the gel discussed previously for unit 10, the jar preferably contains simply frozen water initially. This gives the user the flexibility to take ice or cold water from the jar for a drink or other purpose at any time during use of the unit 100.

Although the present invention has been described with respect to specific preferred embodiments thereof, various changes and modifications can be suggested to one skilled in the art and it is intended that the present invention encompass such changes and modifications as fall within the scope of the appended claims.

I claim:
1. A portable cooling unit, comprising:
a case defining a passage therethrough opening to the ambient air at an inlet and an outlet;

a first cold object having a temperature less than the temperature of the ambient air positioned in the passage;

a second cold object having a temperature less than the temperature of the ambient air positioned in the passage;

the passage being configured so that air flowing through the passage from the inlet first passes the first cold object and subsequently passes the second cold object;

a fan to force ambient air through the passage from the inlet, past the cold objects and from the outlet; and first, second and third cold objects, and at least four aluminum baffles mounted in the case to define the passage, the air flow passing over each of the cold objects sequentially, the aluminum baffles assisting the cooling of the air by conduction and convection.

2. A portable cooling unit, comprising:

a case to finding a passage therethrough opening to the ambient air at an inlet and an outlet, the passage defining first, second and third chambers connecting one to the other in a series relationship;

first, second and third cold objects having a temperature less than the temperature of the ambient air, said first cold object positioned in said first chamber, said second cold object positioned in said second chamber, and said third cold object positioned in said third chamber;

a fan to force ambient air through the passage from the inlet, through the first, second and third chambers sequentially and from the outlet; and sides, and two open ends, said first cold object resting on the top of said baffle, said case and the top of said baffle forming said first chamber, said second gold object resting on the bottom of said baffle within the baffle, the top, bottom and sides of the baffle forming the second chamber.

3. The portable cooling unit of claim 2 further comprising a second heat conductive baffle, the third cold object resting on the second heat conductive baffle, the bottom of said first heat conductive baffle, the case and said second heat conductive baffle forming third chamber.

4. A portable cooling unit, comprising:

a case defining a passage therethrough opening to the ambient air at an inlet and an outlet, the passage defining first, second and third chambers connecting one to the other in a series relationship;

first, second and third cold objects having a temperature less than the temperature of the ambient air, said first cold object positioned in said first chamber, said second cold object positioned in said second chamber, and said third cold object positioned in said third chamber;

a fan to force ambient air through the passage from the inlet, through the first, second and third chambers sequentially and from the outlet, and the first, second and third chambers lie one atop the other, the inlet opening into the uppermost chamber so that as the air is cooled, the increased density of the air creates a natural convection flow supplementing the flow induced by the fan.

* * * * *

UNITED STATES PATENT AND TRADEMARK OFFICE
CERTIFICATE OF CORRECTION

PATENT NO. : 5,046,329
DATED : September 10, 1991
INVENTOR(S) : Travis, III

It is certified that error appears in the above-identified patent and that said Letters Patent is hereby corrected as shown below:

Column 1, line 29, delete "dearly" and insert therefore --clearly--.

Column 2, line 20, delete --10--.

Column 5, line 33, after the second "and", insert therefore --a first heat conductive metal baffle having a top, a bottom, two--.

Signed and Sealed this

Thirteenth Day of July, 1993

Attest:

MICHAEL K. KIRK

Attesting Officer

Acting Commissioner of Patents and Trademarks